(12) United States Patent  (10) Patent No.: US 7,503,605 B2
Mears  (45) Date of Patent: Mar. 17, 2009

(54) CONTACT LENS MANIPULATION AND CLEANING APPARATUS

(75) Inventor: Lee Mears, Framlingham (GB)

(73) Assignee: Principal Design (UK) Limited (GB)

( * ) Notice: Subject to any disclaimer, the term of this patent is extended or adjusted under 35 U.S.C. 154(b) by 384 days.

(21) Appl. No.: 10/560,261

(22) PCT Filed: Jun. 11, 2004

(86) PCT No.: PCT/GB2004/002506

§ 371 (c)(1),
(2), (4) Date: Dec. 9, 2005

(87) PCT Pub. No.: WO2004/108032

PCT Pub. Date: Dec. 16, 2004

(65) Prior Publication Data

US 2006/0131904 A1  Jun. 22, 2006

(30) Foreign Application Priority Data

Jun. 11, 2003 (GB) ................................. 0313475.6

(51) Int. Cl.
A61F 9/00 (2006.01)
(52) U.S. Cl. ....................................................... 294/1.2
(58) Field of Classification Search .................. 294/1.2; 206/5.1; 606/107
See application file for complete search history.

(56) References Cited

U.S. PATENT DOCUMENTS 3,091,328 A  5/1963  Leonardos
3,600,028 A  8/1971  Henning
3,743,337 A * 7/1973  Crary .......................... 294/1.2
3,910,618 A * 10/1975  Massenz ..................... 294/1.2
4,026,591 A  5/1977  Cleaveland
4,093,291 A  6/1978  Schurgin
4,201,408 A  5/1980  Tressel
4,378,126 A * 3/1983  Procenko .................... 294/1.2
4,427,226 A  1/1984  Shartzer
5,236,236 A  8/1993  Girmont
6,739,636 B2 * 5/2004  Py ............................... 294/1.2
2002/0163212 A1  11/2002  Py

FOREIGN PATENT DOCUMENTS

EP  0778656  6/1997

OTHER PUBLICATIONS

International Search Report of PCT/GB04/002506.

* cited by examiner

*Primary Examiner*—Dean J Kramer
(74) *Attorney, Agent, or Firm*—Bourque & Associates, PA

(57) ABSTRACT

The present invention provides apparatus for manipulating and cleaning of contact lenses, together with methods for same. The apparatus comprises at least one eyepiece, at least one body and a cleaning housing. The at least one eyepiece is attached to the at least one body and defines an opening in the body. The at least one eyepiece comprises a head for engaging a contact lens and an eyelid opening mechanism. The at least one body includes a contact tens manipulation device. The apparatus is arranged such that when the at least one eyepiece is attached to the body and the face of the user is in contact with the eyepiece, the eyelid opening mechanism engages the upper and lower eyelids to retain them open while a retractable mechanism removes the contact lens from the eye of the user. The cleaning housing is engageable with the eyepiece and can effectuate cleaning of the contact lens once removed from the eye of the user.

15 Claims, 6 Drawing Sheets

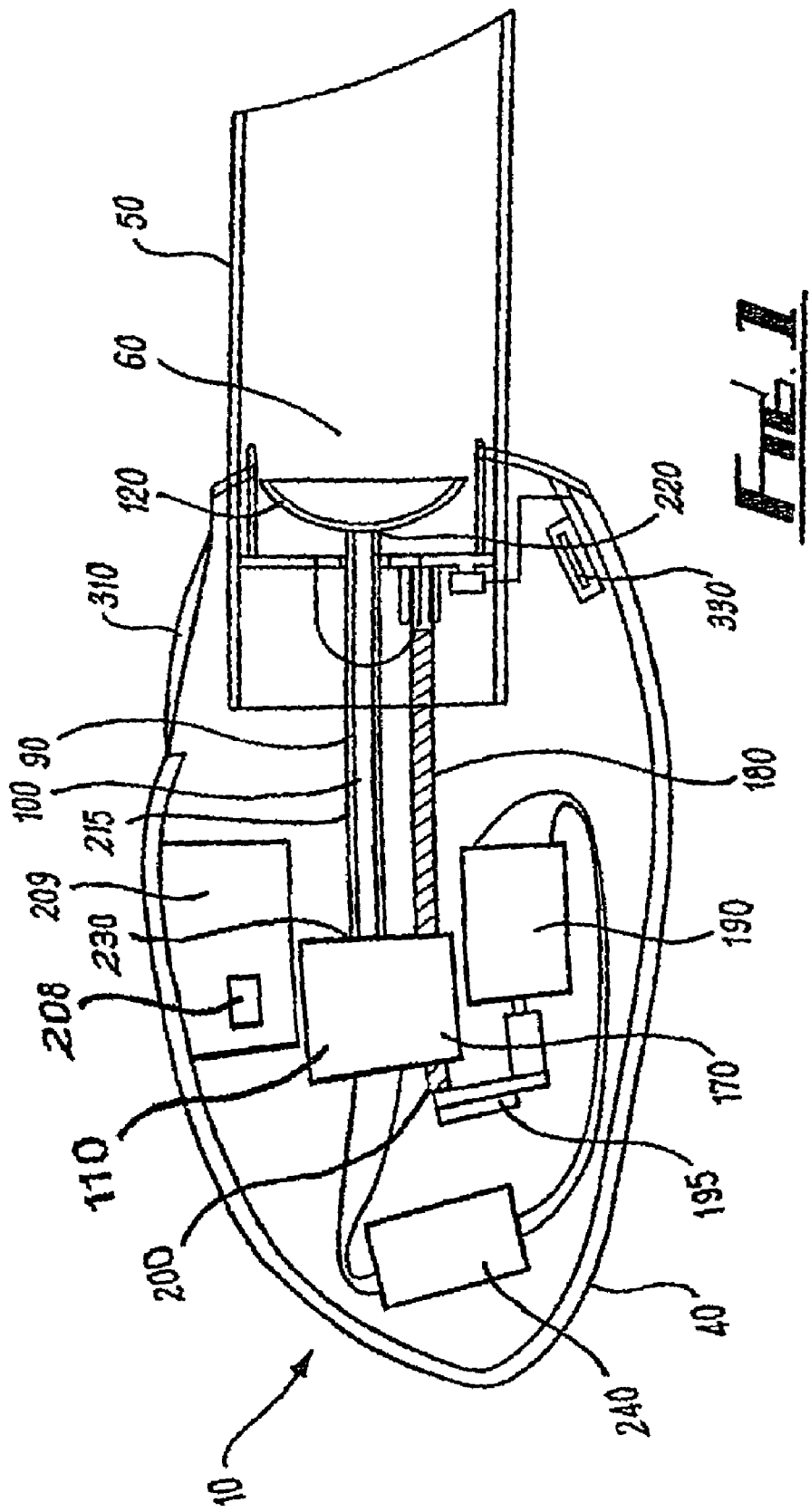

CONTACT LENS MANIPULATION AND CLEANING APPARATUS

TECHNICAL FIELD

This invention relates to an apparatus for hygienic insertion, positioning and removal of contact lenses from a person's eyes.

BACKGROUND INFORMATION

It is estimated that more than 150 million people in the USA use corrective eye wear for refractive errors (Prevent Blindness America, 2002). Contact lenses represent an increasingly popular and convenient solution to correct defective vision such that the contact lens market has a growth of approximately 20% year over year, and sales have grown from $16 million in 1998 to an expected $184 million in 2003. Contact lenses by their very nature are small, delicate and easily damaged, and this leads to problems associated with handling and insertion for a great many users. Installation and removal of contact lenses can be physically cumbersome and time consuming, and the majority of users are known to experience difficulties when they first start wearing contact lenses.

Many people go on to find the insertion and removal of contact lenses a natural thing to do, but a significant proportion of people are believed to have continuing difficulties/problems associated with contact lens insertion/removal. It is widely perceived within the industry that there is a requirement for a solution to overcome the problems associated with manipulation, insertion and removal of contact lenses.

Hygiene can also pose a problem with regard to the wearing of contact lenses-in the event that a contact lens is dropped during insertion into or removal from the eye it may become contaminated with particulate matter (e.g. dirt) or microorganisms (e.g. bacteria), which can cause infections, discomfort, and damage to the eye. There is also a risk that a contact lens may become contaminated through contact with the skin of a finger or the palm of the hand. A variety of microorganisms are involved in causing eye infections, but the most commonly isolated organisms are Serratia, Pseudomonas and Acinetobacter (from contaminated sterilizing and washing solutions) and staphylococci (from direct handling of contact lenses). In order to maintain good ocular hygiene it is important that a contact lens user washes their hands prior to insertion/removal of a contact lens, and that the contact lenses are cleaned properly in accordance with the manufacturers instructions.

Indeed, deviation from recommended wear and care procedures are the prime factors involved in contraction of Acanthamoeba keratitis, a serious and painful condition which may cause long-term damage to the eye. Cleaning and disinfection of contact lenses can thus be time consuming and impractical, particularly when a user does not have a ready means available to clean their hands prior to handling their contact lenses e.g. whilst travelling. Survey evidence suggests that 75% of existing contact lens users reported that they would use an apparatus which would not only insert/remove their lenses but also clean and store them.

Prior art contact lens insertion and removal devices include U.S. Pat. No. 4,201,408, U.S. Pat. No. 4,427,226, and WO 99/21519. U.S. Pat. No. 4,201,408 discloses a device having a cup to receive a contact lens, the cup having a hole connected to a tube. The tube serves to apply negative pressure to the contact lens in order to pick it up, and positive pressure to facilitate discharge of the contact lens onto the eyeball. The tube also provides a light source, visualized as a bright spot of light which can serve as a target by a user, thereby making the process of contact lens insertion/removal easier. A means is provided to distort the cup and the contact lens which aids removal of a contact lens from the eye.

U.S. Pat. No. 4,427,226 discloses a device combining a means to position or remove a contact lens combined with a means to keep the upper and lower eyelids open. Using one hand, the eyelids are retained open using eyelid engaging means, and the contact lens is positioned or removed using the other hand and a pair of flexible tweezers.

WO 99/21519 discloses a package containing a contact lens stored in saline solution. The package comprises an applicator for applying the contact lens to the eye, thereby circumventing the requirement for a user to physically pick up the contact lens and place it on their palm prior to insertion onto the eyeball. By removing contact between fingers and the contact lens, the chances of contaminating the contact lens by a user are thereby considerably reduced, and good ocular hygiene is maintained.

Prior art devices are primarily used for the insertion and/or removal of contact lenses from the eye. The devices, although minimizing contact with skin and therefore the risks of contamination of a contact lens, still require the use of both hands, typically with one hand holding open the eyelids, and the other hand inserting the contact lens through the use of an applicator or tweezers. The application step, although facilitated through the use of tweezers or an applicator, can still be problematic since it invariably requires a degree of skill and dexterity by the user-a good aim and appropriate use of force is required to position a contact lens on the eyeball. Importantly, none of the prior art devices are designed for cleaning contact lenses—the contact lenses may be removed and stored using the prior art devices, but cleaning of a contact lens prior to storage invariably involves manual (i.e. fingertip) "scouring" or "scrubbing" of the contact lens with a cleaning solution typically comprising a detergent followed by rinsing with a sterile saline solution.

SUMMARY

It is an object of the present invention to overcome the prior art disadvantages by providing an apparatus for use with a contact lens which comprises automatic contact lens installation, insertion, removal, manipulation, cleaning, and storage steps, without the need for a user to physically manipulate or clean the contact lens themselves.

According to a first aspect of the present invention there is provided an apparatus for manipulation and cleaning of a contact lens, said apparatus comprising an at least one eyepiece, an at least one body, and a cleaning housing, said at least one eyepiece when attached to said at least one body defining an opening into said at least one body and said at least one eyepiece comprising:

(i) a head for engaging a contact lens; and
(ii) an eyelid opening means, said at least one body containing a contact lens manipulation means comprising an elongate arm defining a longitudinal axis and an arm movement means communicating with said arm, said arm movement means effecting movement of said arm between a retracted position and an extended position;

said apparatus arranged such that when said at least one eyepiece is attached to said at least one body and the face of a user is in contact with said at least one eyepiece, an eyeball and upper and lower eyelids of said user being positioned over said opening, said eyelid opening means is engageable with said upper and lower eyelids to retain them open, said arm being engaged with said head and being extendable to contact said eyeball of said user and effect insertion and removal of a contact lens into and from said eye;

said cleaning housing comprising contact lens cleaning means and being engageable with said at least one eyepiece, such that when said at least one eyepiece and said cleaning housing are engaged, said contact lens cleaning means can effect cleaning of a contact lens engaged with said head of said at least one eyepiece.

The at least one eyepiece may be removeably attachable to the at least one body.

Alternatively the at least one eyepiece may be permanently engaged with the at least one body.

Thus, the apparatus may comprise one eyepiece attached to one body, and a cleaning housing which is engageable with the eyepiece.

The at least one eyepiece may define an opening into the body and an eyehole. A user may position their eye over the eyehole and look into the eyehole.

The at least one eyepiece may be adapted such that when the face of a user is in contact with the eyepiece, external light is not visible to the user, e.g. is prevented from entering between the face of the user and the eyepiece, thus being prevented from entering the volume defined by the person's face, the eyepiece and the body. The at least one eyepiece may extend around the eyelid opening means, thereby protecting it from damage. The at least one eyepiece may be sprung such that when it is pressed against the face of a user, it retracts towards the body of the apparatus and the eyelids of the user contact the eyelid opening means. The arms may be spaced so as to not contact the eyeball of a user.

The eyepiece or body may comprise a light source such that when a user looks through the eyepiece into the opening of the device, the user sees a small focussed spot of light, thereby preventing the user from seeing the arm and the head of the device. The inability of the user to see the components of the device, both in a static or moving state, minimizes flinching by the user and facilitates insertion and removal of contact lenses. The spot of light may be colored to indicate either normal function or to prompt the user to change the batteries of the device, or their contact lenses. The light may also be used to signal other information to a user.

The apparatus (for example the body) may comprise a control (e.g. a button or switch), for use by a user to control the contact lens manipulation means. By actuating the control, a user can thus install or remove a contact lens into their eye, or remove a contact lens from its packaging and install it into the apparatus. All the functions of the apparatus may be controlled through the use of the control.

The apparatus may comprise two eyepieces, two bodies, and a cleaning housing, each eyepiece being attached to a body, the cleaning housing being engageable with the eyepieces. Each eyepiece may define an opening into the body, and may comprise a head for engaging a contact lens and an eyelid opening means. The body may comprise a contact lens manipulation means, wherein when the face of a user is in contact with the eyepiece, an eyeball and upper and lower eyelids of the user being positioned over the opening, the eyelid opening means is engageable with the upper and lower eyelids to retain them open, the contact lens manipulation means comprising an elongate arm defining a longitudinal axis and an arm movement means communicating with the arm, the arm movement means effecting movement of the arm between a retracted position and an extended position; wherein when the at least one eyepiece is attached to the at least one body and the face of a user is in contact with the at least one eyepiece, an eyeball and upper and lower eyelids of the user being positioned over the opening, the eyelid opening means can engage the upper and lower eyelids and retain them open, the arm engaged with the head extending to contact the eyeball of the user and effect insertion and removal of a contact lens into and from the eye;

the cleaning housing comprising contact lens cleaning means and being engageable with the at least one eyepiece, such that when the at least one eyepiece and the cleaning housing are engaged, the contact lens cleaning means can effect cleaning of a contact lens engaged with the head of the at least one eyepiece.

The apparatus may comprise two eyepieces, one body and a cleaning housing, the eyepieces being removeably attachable to the body and the cleaning housing being engageable with the eyepieces, such that when at least one eyepiece is engaged with the cleaning housing, the contact lens cleaning means can effect cleaning of any contact lens engaged with the head of the eyepiece.

The apparatus may be formed such that only one of the two eyepieces is attachable to the body at any given time.

The arm may be capable of releasably engaging the head.

The arm may extend through the opening to engage the head.

The arm movement means may effect movement of the arm between a retracted position in which the arm is contained within the body of the apparatus, and an extended position in which the arm extends through the opening.

The arm may be attached to the head. The eyepieces may each hold a contact lens, the prescription of which corresponds to a particular eye. The eyepieces may be formed so that one eyepiece has a shape adapted for use with the left eye of a user, and the other eyepiece has a shape adapted for use with the right eye. The shape of an eyepiece may be such that if it is attempted for use with the incorrect eye, an incorrect fit is made which is noticeable to the user. This prevents insertion into the eye of a contact lens of the wrong shape or prescription.

The eyelid opening means may comprise a plurality of arms, each of the arms being movable within a guide track positioned within the eyepiece, wherein the arms, responsive to contact against the upper and lower eyelids of a user, move along the guide tracks engaging and retaining the upper and lower eyelids in an open position.

The contact lens manipulation means may comprise a rack associated with the arm, the rack engaging with a worm associated with the arm movement means. Movement of the rack is responsive to rotational movement of the worm about it's longitudinal axis. The use of rack and worm gears will be well known to a person skilled in the art. The contact lens manipulation means may comprise an electric motor to effect movement of the arm between extended and retracted states. Movement of the arm is not limited to the use of a rack and worm-indeed, other ways of moving the arm are envisaged and will be well known to a person skilled in the art. In particular, the arm movement means may comprise apparatus described in EP 0784252 (also known in the art as "SMAC" devices/technology), effecting actuation of the arm and in particular to effecting a "soft landing" of the head (and thus of a contact lens when engaged with the head) on the eye of a user. Actuators, spring arrangements and other devices described in EP 0635786 and EP 0778656 may also be used.

The apparatus, particularly the eyepiece, may be provided with a fluid drainage arrangement in order to allow fluid such as contact lens cleaning fluid to be drained from the eyepiece, preventing its damaging the apparatus contained in the body. For example, the at least one eyepiece may be provided with fluid drainage means. In addition, seal means may be provided (for example incorporated into the at least one eyepiece and/or into the at least one body) preventing the transmission of fluid from the at least one eyepiece into the at least one body. This can allow movement of the arm without allowing the transmission of fluid.

The head may be resiliently deformable, defining a first extended position, and a second contracted position, wherein the head is capable of gripping a contact lens when the head is in the second position. The head of the eyepiece may be shaped to complement the shape of a contact lens (e.g. cup shaped), and/or it may comprise a plurality of gripping arms e.g. two, three or four arms. The head may be manufactured from a resiliently deformable material, e.g. a low shore factor thermoplastic elastomer (TPE). The head and gripping arms may be moulded to facilitate gripping or pinching of a contact lens when the head is in the second (contracted) position.

The contact lens manipulation means may comprise a head manipulating means to effect gripping of a contact lens by the head of the eyepiece, to facilitate removal of a contact lens from the eye or its packaging.

The head manipulating means may comprise a longitudinally elongate sleeve positioned coaxial with and radially extended from the arm and defining first and second ends, the arm being positioned radially inwards of the sleeve and defining a head-contacting end, the first end of the sleeve terminating adjacent to the head-contacting end of the arm, wherein the head and arm are movable relative to the sleeve along the longitudinal axis between a first position in which the head does not engage the sleeve and is in the first extended state, and a second position in which the head engages the sleeve and is deformed into the second contracted state, thereby effecting gripping of the contact lens.

The sleeve and the arm may be reversibly coupled to one another. The head manipulating means may comprise a coupling control means, the coupling control means being capable of coupling and uncoupling the sleeve and the arm between coupled and uncoupled states.

In the coupled state the arm moves in conjunction with the sleeve, and in the uncoupled state the arm moves independently of the sleeve.

The coupling control means may be electronic or electromagnetic (for example a solenoid).

The coupling control means may be preferably operatively linked to the arm movement means, and controlled such that the sleeve and arm are automatically uncoupled when the head of the arm contacts a contact lens placed in position on the eyeball, prior to retraction of the arm and gripping of the contact lens. Retraction of the arm through the sleeve need only be a short distance, for example between 0.3-2.0 cm. Retraction of the arm may be controlled in order to avoid the head and contact lens being pulled through the first end of the sleeve and damaged.

The contact lens cleaning means may comprise an at least one cleaning arm defining a cleaning head capable of contacting a contact lens, and a cleaning arm movement means communicating with the cleaning arm, the cleaning arm movement means effecting movement of the cleaning head for cleaning a contact lens. The contact lens cleaning means may comprise two cleaning arms, each arm being capable of cleaning a contact lens contained within an eyepiece.

The cleaning arm movement means may comprise an electric motor to effect rotational movement of the cleaning arm about it's longitudinal axis, and may be provided with an off centre gear which provides a vertically oscillating movement.

The contact lens cleaning means may comprise an ultrasonic cleaning means, for example an ultrasonic probe. Ultrasonic cleaning devices are well known to a person skilled in the art.

The contact lens cleaning means may be turned on or off or otherwise controlled by way of a control (e.g. a switch or button) located on the cleaning housing, and a user can thus clean contact lenses contained within the eyepieces by actuating the control.

The apparatus (for example the cleaning housing) may comprise a compartment for storage of contact lens cleaning solutions and/or other components. The body and cleaning housing may comprise a compartment in which batteries may be stored, the batteries being used to power the apparatus.

The present invention in its various aspects also provides the opportunity to incorporate medical testing equipment for testing at least one eye of a patient. For example the apparatus may incorporate equipment to test a patient for glaucoma. Visual field test means may be incorporated into the apparatus, enabling a visual field test to be performed using it. For example, at least part of the visual field test means may be incorporated into the body of the apparatus. The visual field test means could be provided in the form of equipment for operation by a qualified optician or physician, or could be in the form of equipment for home use and which in the case of an adverse result being obtained can advise a user to seek medical advice to determine whether they are suffering from glaucoma. Other testing equipment is well known in the art and can be incorporated with the apparatus of the present invention. In particular, the present invention is well suited to testing equipment which requires clear access to at least one eye of a patient.

The apparatus can also provide convenient means for advising a user regarding the changing of contact lenses. For example, the apparatus may be adapted such that after a pre-defined number of insertions and removals of a given contact lens the user is advised (for example by the displaying of a message or lighting up of a warning light) that the contact lens needs replacing. As discussed below, messages may be displayed to a user (for example by way of a colored light) during use of the apparatus. Alternatively, instead of determining whether a pre-defined number of insertions and removals has been performed, a message may be displayed when a certain period of use (e.g. one week or one month) of a lens has elapsed. The apparatus may be provided with data input means to allow the setting and re-setting of necessary information, for example the start date of use of a lens or the number of uses of a lens. The apparatus may additionally be adapted such that for example in the case where multiple heads are to be used with one body, each head can be distinguished by the body and messages appropriate to that head issued. Alternatively, a head may contain within it the means for determining its use and issuing messages etc.

According to a second aspect of the present invention there is provided a method of inserting or removing at least one contact lens into or from an eye of a user using an apparatus for manipulation of a contact lens, said apparatus comprising an at least one eyepiece and an at least one body, said at least one eyepiece when attached to said at least one body defining an opening into said at least one body and said at least one eyepiece comprising:

(i) a head for engaging a contact lens; and
(ii) an eyelid opening means, said at least one body containing a contact lens manipulation means comprising an elongate arm defining a longitudinal axis and an arm movement means communicating with said arm, said arm movement means effecting movement of said arm between a retracted position and an extended position;

said apparatus arranged such that when said at least one eyepiece is attached to said at least one body and the face of a user is in contact with said at least one eyepiece, an eyeball and upper and lower eyelids of said user being positioned over said opening, said eyelid opening means is engageable with said upper and lower eyelids to retain them open, said arm being engaged with said head and being extendable to contact said eyeball of said user and effect insertion and removal of a contact lens into and from said eye;

said method comprising the steps of: (i) contacting the face of a user with said at least one eyepiece, an eyeball and upper and lower eyelids of the user being positioned over said opening; (ii) operating said apparatus so as to engage said upper and lower eyelids and retain them open and extend said arm engaged with said head to contact said eyeball of said user and effect insertion or removal of a contact lens into or from said eye.

Also provided is a method of inserting or removing at least one contact lens according to the second aspect of the present invention, the apparatus additionally comprising a cleaning housing comprising contact lens cleaning means and being engageable with the eyepiece, such that when the at least one eyepiece and cleaning housing are engaged, the contact lens cleaning means can effect cleaning of a contact lens engaged with the head of the eyepiece, the method additionally comprising the steps of:

(i) engaging the cleaning housing with the at least one eyepiece having a contact lens engaged with the head;
(ii) operating the apparatus so as to effect cleaning of a contact lens engaged with the head of the eyepiece.

The various aspects and features of the apparatus of the present invention equally apply to the methods of the present invention.

BRIEF DESCRIPTION OF THE DRAWINGS

The invention will now be described by way of example only with reference to the accompanying drawings in which:

FIG. 1 shows a shows a sectional view of the apparatus according to the present invention;

DETAILED DESCRIPTION OF THE PREFERRED EMBODIMENTS

Figure 5C:
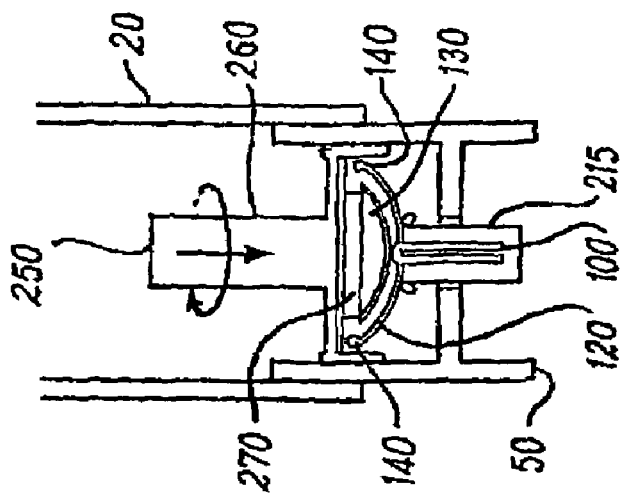
FIG. 5 shows a side view of the stages in the cleaning of a contact lens contained within the apparatus according to the present invention, (a) prior to addition of cleaning solution, (b) after addition of cleaning solution, and (c) during cleaning of the contact lens by the contact lens cleaning means.
Figure 5B:
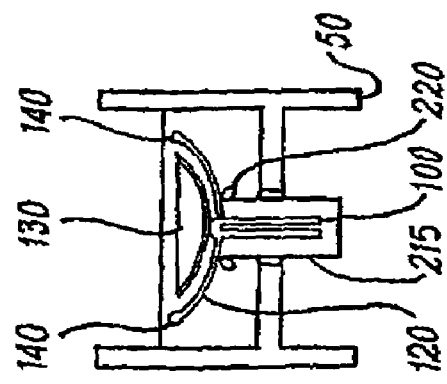
Figure 5A:
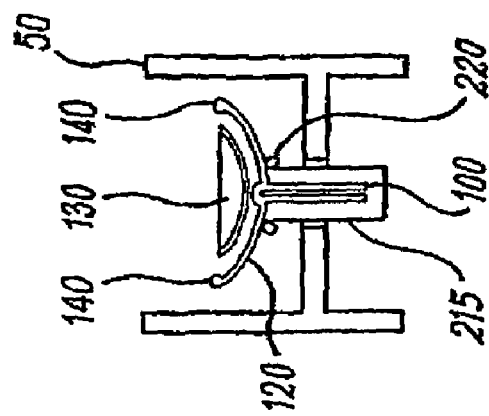

In a first embodiment of the invention, the apparatus 10 comprises two eyepieces 50 which are removeably attachable to a body 40 (FIG. 1). Only one of the eyepieces 50 may be attached to the body 40 at any given time. The eyepieces 50 are also releasably engageable with a cleaning housing 20 (FIG. 5C). Each eyepiece 50, when attached to the body 40, defines an opening 60 into the body 40 of the apparatus 10.

In a second embodiment of the invention, the apparatus 10 comprises two eyepieces 50, two bodies 40 and a cleaning housing 20, wherein each of the eyepieces 50 is attached to a body 40. The eyepieces 50 are also releasably engageable with a cleaning housing 20.

Each eyepiece 50 defines an opening 60 into the body 40 of the apparatus 10.

Figure 2A:
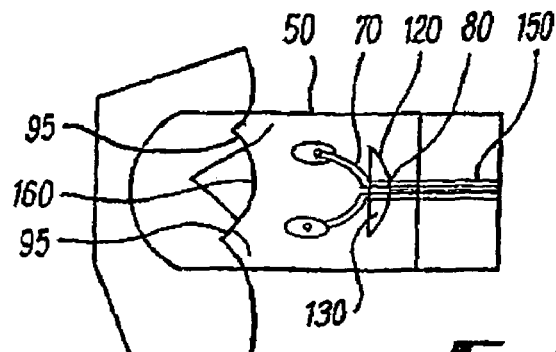
FIG. 2 shows a sectional view of the eyelid opening means contained within the eyepiece of the apparatus, (a) prior to contact with the eyelids of a user, (b) contacting the eyelids of a user, and (c) retaining the eyelids of a user in an open position.
Figure 2B:
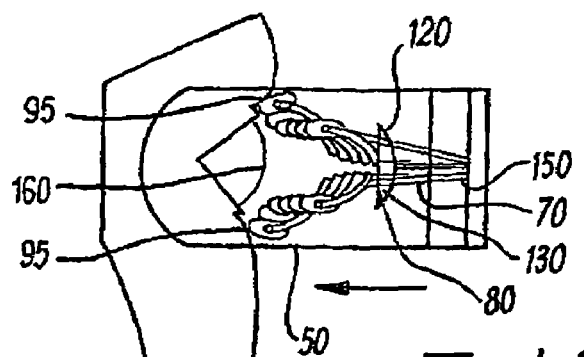
Figure 2C:
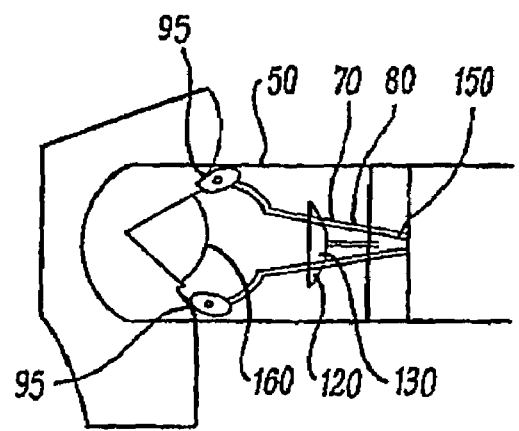

The eyepieces 50 each comprise an eyelid opening means 70 and a head 120 for engaging a contact lens 130 (FIG. 2). The eyelid opening means 70 comprises a plurality of eyelid opening arms 80, each of the eyelid opening arms 80 being movable within a guide track 150 positioned within the eyepieces 50, wherein the eyelid opening arms 80, responsive to contact against the upper and lower eyelids 95 of a user (FIG. 2A), move along the guide tracks 150 (FIG. 2B) engaging and retaining the upper and lower eyelids 95 in an open position (FIG. 2C). The eyepieces 50 of the apparatus 10 extend around the eyelid opening means 70, thereby protecting it from damage. The eyepiece 50 is sprung such that when it is pressed against the face of a user, the eyepiece 50 retracts towards the body 40 of the apparatus 10 and the eyelids 95 of the user contact the eyelid opening means 70.

Arms 80 are spaced so as to not contact the eyeball 160 of a user. The eyelid opening means 70 serves to prevent blinking during insertion and removal of a contact lens 130.

The head 120 of the eyepiece 50 can engage a contact lens 130.

With the face of a user in contact with eyepiece 50, the user is prevented from seeing external light (i.e. light is prevented from entering between the face of the user and the eyepiece).

Figure 3:
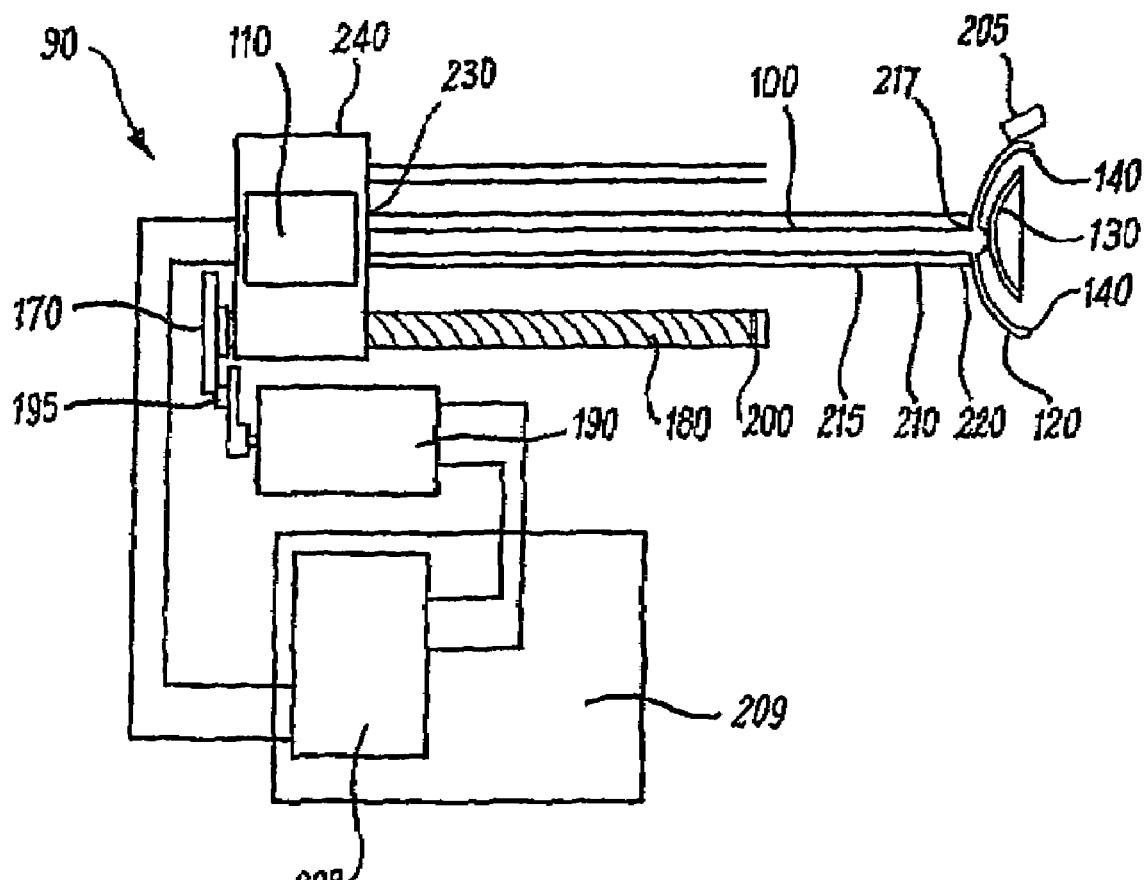
FIG. 3 shows a plan view of the contact lens manipulation means of the apparatus with the arm contacting the head of the eyepiece.

The body 40 comprises a contact lens manipulation means 90 (FIG. 3) comprising an elongate arm 100 defining a longitudinal axis and an arm movement means 110, communicating with the arm 100. The arm 100 can engage with the head 120 contained within the eyepiece 50. The arm movement means 110 is capable of effecting movement of the arm 100 between a retracted position, wherein the arm 100 is contained within the body 40 and an extended position, wherein the arm 100 extends through the opening 60, engages with the head 120 contained in the eyepiece 50, and causes the head 120 to contact the eyeball 160 of the user and effect insertion and removal of a contact lens 130 into and from an eye (FIG. 3).

Each eyepiece 50 or body 40 comprises a light source (not shown) such that when a user looks through the eyepiece 50 into the opening 60 of the apparatus 10, the user sees a small focussed spot of light, thereby preventing the user from seeing the arm 100 and the head 120 of the apparatus 10. The inability of the user to see the components of the apparatus 10, both in a static or moving state minimizes flinching by the user and facilitates insertion and removal of contact lenses. The spot of light can be colored to indicate either normal function or to prompt the user to change the batteries of the device, or their contact lenses.

The contact lens manipulation means 90 comprises a rack 170 associated with the arm 100, the rack 170 engaging with a worm 180 associated with the arm movement means 110.

The contact lens manipulation 90 means comprises an electric motor 190 to effect movement of the arm 100 between extended and retracted states. A plurality of gears 195 are provided to improve the control of the arm 100 and the range of speed available for extension and retraction of the arm 100.

The arm 100 travels along the worm 180 in either direction responsive to rotation of the worm 180 about it's longitudinal axis in one or other direction. Movement of the arm 100 along the worm 180 in one direction corresponds to extension of the arm 100 such that the head 120 extends through the opening 60, and movement of the arm 100 in the other direction along the worm 180 corresponds to retraction of the arm 100, such that it is fully contained within the body 40 of the apparatus 10. The worm 180 is provided with a stop 200 at one or both ends to limit movement of the arm 100. The arm 100 may be extended and retracted through the opening 60 of the apparatus 10 by traveling along the worm 180, and the extension and retraction can be controlled by a user. In one embodiment of the invention (see FIG. 3), the head 120 of each eyepiece 50 comprises a laser reader 205 which accurately measures the distance between the eyeball 160 (i.e. the point of contact) and the head 120 of the eyepiece 50. The apparatus 10 is fitted with a chip 208 located on a circuit board 209 which controls movement of the arm 100 in response to this measured distance approaching a set parameter. At this point the apparatus 10 moves the arm 100 in a tightly controlled and precise way, thereby inserting the contact lens 130 into the eye in an extremely accurate and safe manner. Movement of the arm 100 along the worm 180 is in response to operation of the apparatus 10 by a user. Apparatus 10 comprises a button 310 (FIG. 1) located on the body 40 to be depressed by a user in order activate movement of the arm 100.

The same apparatus 10 fitted with a laser reader 205, which measures the distance between the eyeball 160 and the head 120 of the eyepiece 50 in real time, is useable by a multitude of users, for example, all the members of a family who wear contact lenses. In one embodiment of the invention, the apparatus 10 is fitted with a chip 208 which contains the precise measurements for extension of the arm 100, as determined by e.g. an optician, such that the apparatus 10 can quickly and safely insert a contact lens 130 into the eye of a user, and that user can have the utmost confidence that the apparatus 10 can insert a contact lens 130 safely, since the apparatus 10 is tailored to insert a contact lens 130 in accordance with precise measurements of their facial and eye anatomy.

The head 120 of each eyepiece 50 is resiliently deformable, defining first extended, and second contracted positions, wherein the head 120 is capable of gripping a contact lens 130 when the head 120 is in the second position. The head 120 of each eyepiece 50 is cup shaped to complement the shape of a contact lens 130 or comprises a plurality of gripping arms 140 e.g. two, three or four. Head 120 is manufactured from a resiliently deformable material such as a low shore factor thermoplastic elastomer (TPE). The head 120 and gripping arms 140 are moulded to facilitate gripping or pinching of a contact lens 130 when the head 120 is in the second (contracted) position.

Figure 4A:
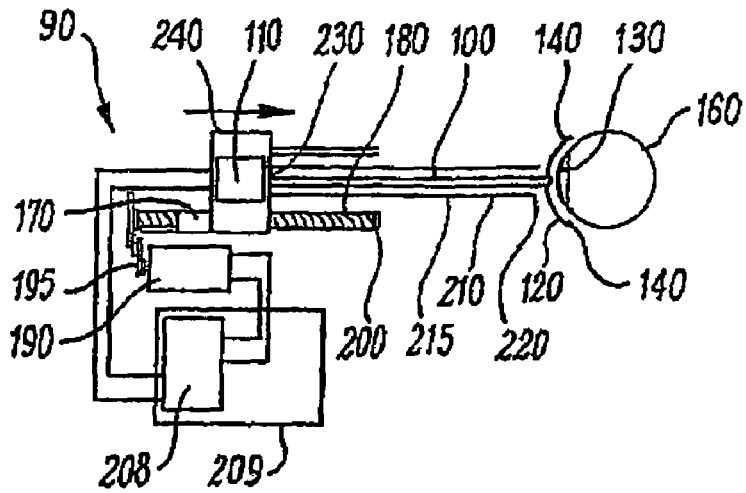
FIG. 4 shows a side view of the stages in the removal of a contact lens from an eye, (a) at the moment when the head of the eyepiece contacts the contact lens, (b) retraction of the arm/sleeve and uncoupling of the sleeve and arm, (c) retraction of the arm relative to the sleeve causing deformation of the head and effecting gripping of the contact lens by the head, and (d) coupling of the arm and sleeve and retraction of the coupled arm/sleeve into the body.
Figure 4B:
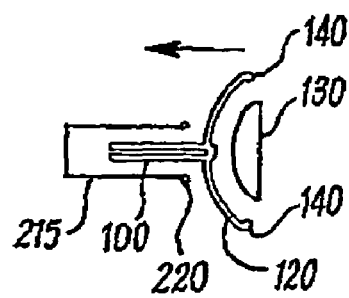
Figure 4D:
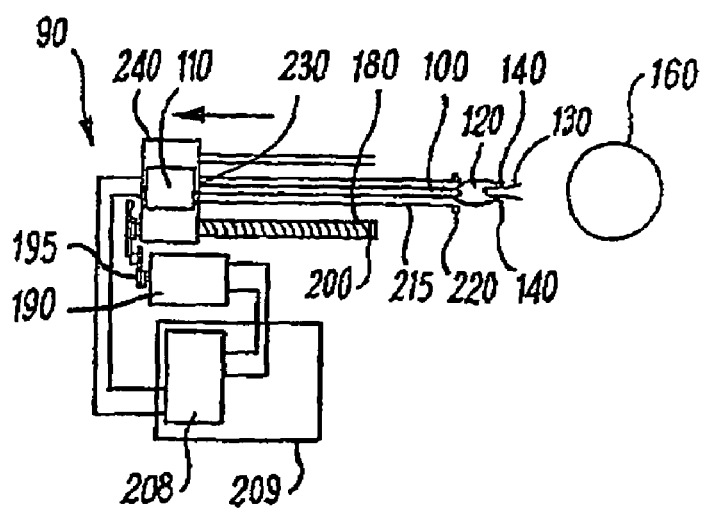
Figure 4C:
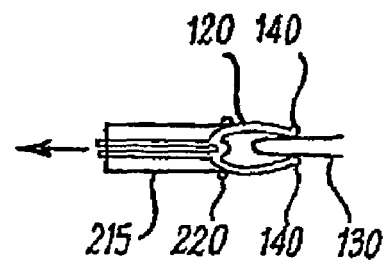

The contact lens manipulation means 90 comprises a head manipulating means 210 to effect gripping of a contact lens 130 by the head 120 of an eyepiece 50, to facilitate removal of a contact lens 130 from the eye or its packaging. The head manipulating means 210 comprises a longitudinally elongate sleeve 215 positioned coaxial with and radially extended from the arm 100. The sleeve 215 defines first and second ends 220,230, the arm 100 being positioned radially inwards of the sleeve 215 and defining a head-contacting end 217, the first end 220 of the sleeve 215 terminating adjacent to the head-contacting end 217 of the arm 120. The head 120 and arm 100 are movable relative to the sleeve 215 along the longitudinal axis between a first position in which the head 120 does not engage the sleeve 215 and is in the first extended state (FIGS. 4A and 4B), and a second position in which the head 120 engages the sleeve 215 and is deformed into the second contracted state, thereby effecting gripping of a contact lens 130 (FIGS. 4C and 4D).

The sleeve 215 and the arm 100 are reversibly coupled to one another and the head manipulating means 210 comprises a coupling control means 240 which is capable of coupling and uncoupling the sleeve 215 and the arm 100 between coupled and uncoupled states. In the coupled state the arm 100 moves in conjunction with the sleeve 215, and in the uncoupled state the arm 100 moves independently of the sleeve 215. When the head 120 contacts the eyeball 160, the sleeve 215 and the arm 100 become uncoupled (FIG. 4B) such that the arm 100 can retract independently of the sleeve 215. Upon retraction of the arm 100, the head 120 contacts the first end 220 of the sleeve 215, and further retraction of the arm 100 causes the first end 220 of the sleeve 215 to deform the head 120 from the first position to the second position and thereby effect gripping of a contact lens 130 (FIG. 4C).

The coupling control means 240 is electronic or electromagnetic. Coupling control means 240 is operatively linked to arm movement means 110 such that sleeve 215 and arm 100 are automatically uncoupled when head 120 contacts a contact lens 130 placed in position on the eyeball 160, prior to retraction of arm 100 and gripping of contact lens 130.

Retraction of arm 100 through sleeve 215 is only a short distance, between 0.3-2.0 cm.

Retraction of arm 100 is controlled so as to prevent head 120 and contact lens 130 being pulled through first end 220 of sleeve 215 and preventing damage. The distance of retraction of arm 100 is sufficient to deform head 120 from a first position to a second position such that contact lens 130 is gripped by head 120, then sleeve 215 and arm 100 are coupled together again, prior to full retraction of coupled arm 100 and sleeve 215 back into body 40 of apparatus 10.

As the coupled arm 100 and sleeve 215 retract into the body 40, the arm 100 disengages from the head 120 leaving it in the eyepiece 50, thereby allowing the head 120 to revert from the second (contracted) position where the contact lens 130 is gripped or pinched, to the first (extended) position, where the contact lens 130 is merely supported by the head 120.

In a second embodiment of the invention, the arm does not disengage from the head. To release the grip on the contact lens, the sleeve 215 is automatically uncoupled from the arm, and the arm 100 extends independently of the sleeve 215 until the head 120 returns from the second (contracted) position, in which the contact lens 130 is gripped, to the first (extended) position, in which the contact lens 130 rests on and is supported by the head 120.

The apparatus comprises a three way micro switch 330 which controls the three modes of action-namely, (i) insertion/removal of a contact lens into or from an eye of a user, (ii) installation of a contact lens into an eyepiece 50, and (iii) removal of a contact lens from an eyepiece 50.

In a first embodiment of the invention, the micro switch 330 is activated by attaching an eyepiece 50 onto the body 40, and securing it in position with clips provided (not shown).

The body 40 can distinguish which eyepiece 50 is being used, where one eyepiece 50 contains a contact lens 130 designed for use with the right eye, and the other eyepiece 50 contains a contact lens 130 designed for use with the left eye. A light or audible signal is relayed to the user to inform them which eye they need to position over the eyepiece 50 in order to install/remove the correct contact lens.

In a second embodiment of the invention, where the eyepieces 50 are each attached to a separate body 40, the micro switch 330 for each body 40 is activated through the use of an external switch positioned on each body 40.

A button 310 is positioned on the external surface of the body 40, for use by a user to control the contact lens manipulation means 90. By depressing the button, a user can thus use the body 40 to e.g. install a contact lens 130 into their eye, or remove a contact lens 130 from its packaging and install it into an eyepiece 50.

The cleaning housing 20 (FIG. 5C) of the apparatus 10 comprises a contact lens cleaning means 250, comprising an at least one cleaning arm 260 defining a cleaning head 270, and a cleaning arm movement means (not shown) communicating with the cleaning arm 260.

The cleaning housing 20 is engageable with eyepieces 50, such that when the cleaning housing 20 is engaged with an eyepiece 50, the contact lens cleaning means 250 can effect cleaning of the contact lens 130 contained within either of the eyepieces 50. The cleaning arm movement means comprises an electric motor (not shown) which is capable of effecting rotational movement of the cleaning head 270 for cleaning a contact lens 130, by effecting rotational movement of the cleaning arm 260 about it's longitudinal axis, and is provided with an off centre gear (not shown) which provides a vertically oscillating movement. Contact lens cleaning means 250 is controlled by switch or button (not shown) located on the cleaning housing 20, and a user can thus clean contact lenses contained within the eyepieces 50 by flicking the switch or pressing the button.

Cleaning housing 20 comprises a compartment for storage of contact lens cleaning solutions and components. The body 40 and cleaning housing 20 comprise a compartment in which batteries may be stored, the batteries being used to power electric motors contained within the apparatus 10.

The body 40, eyepieces 50, and/or cleaning housing 20 of the apparatus 10 comprise at least one compartment for storage of spare contact lenses and cleaning solutions and components. The body 40, eyepieces 50 and cleaning housing 20 are manufactured from injection moulded plastic.

Figure 6:
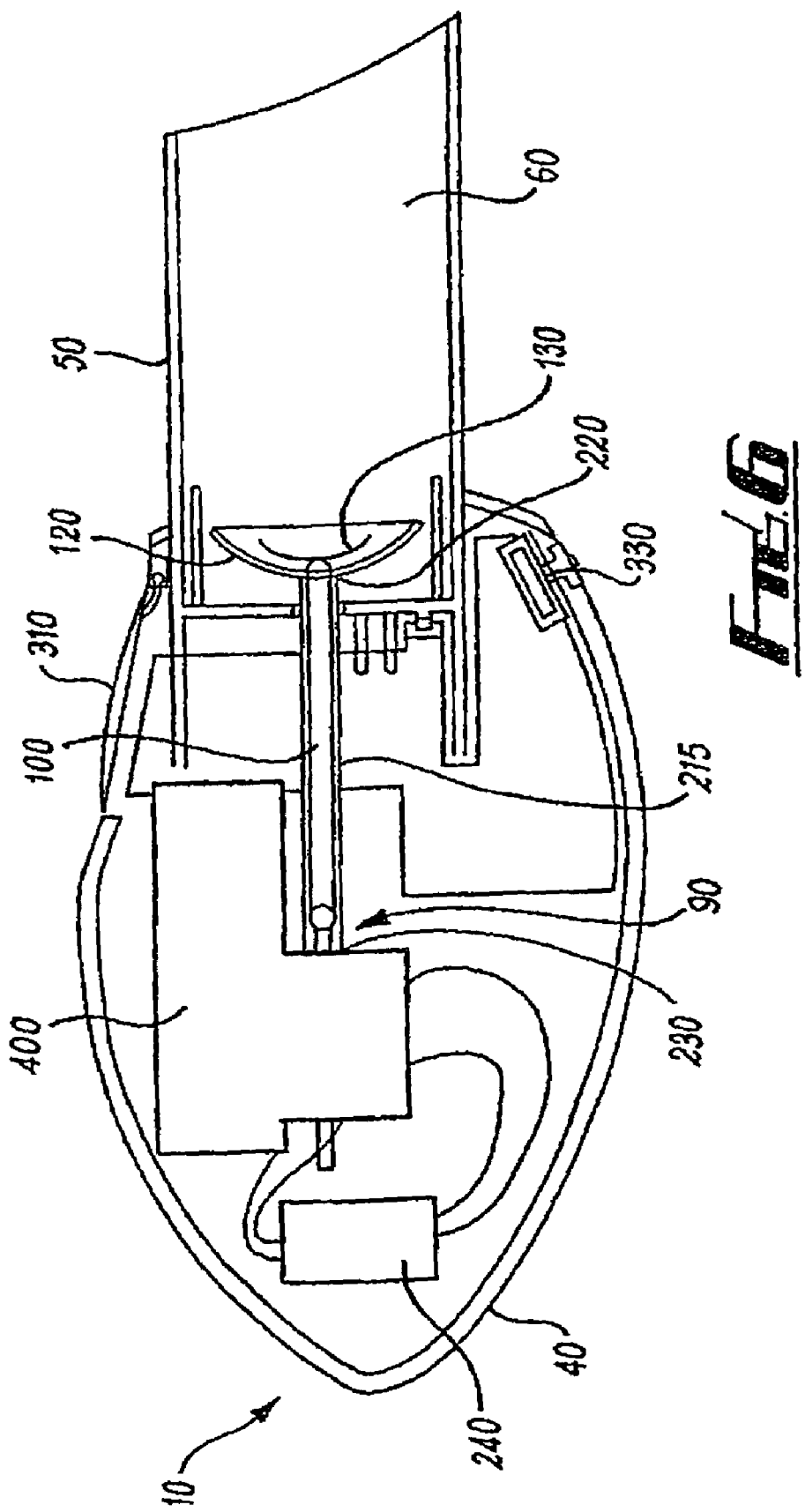
FIG. 6 shows an alternative embodiment to that shown in FIG. 1, with an alternative arm movement means.

As is shown in FIG. 6, in another embodiment of the present invention the contact lens manipulation means 90 comprises an arm movement means 400 comprising an actuator/drive according to EP 0784252, EP 0534786 and EP0778656 which facilitates movement of the arm and the measurement of forces felt against the arm 100 in real time, such that a contact lens 130 may be manipulated with a high degree of precision, and regulated force. When the arm 100 meets a predefined level of resistance, i.e. as it contacts the eyeball 160, it stops quickly and accurately such that there is no risk of the apparatus 10 damaging the eye of a user, thereby enhancing user confidence with the apparatus 10.

EXAMPLES

The following examples detail the various functions that the apparatus 10 according to the present invention can perform.

Removal of Contact Lenses from their Packaging and Installation of Contact Lenses into the Apparatus.

A contact lens 130, immersed within an appropriate storage solution within its packaging can be installed into an eyepiece 50 by pressing the button 310 located on the body 40. A single extended press of the button 310 by a user will trigger the cycle of movements which enable a contact lens 130 to be installed into an eyepiece 50 of the apparatus 10.

The first stage in this cycle is an extension of the arm 100 of the contact lens manipulation means 90 through the opening 60 until the arm 100 engages the head 120 within the eyepiece 50. The arm 100 continues to extend until the head 120 contacts the contact lens 130, at which the point the extension of the arm 100 will precisely stop. Next, the sleeve 215 is automatically uncoupled from the arm, and the arm 100 retracts independently of the sleeve 215 until the head 120 is deformed from the first (extended) position to the second (contracted) position, thereby effecting gripping of the contact lens 130. Then, the arm 100 and the sleeve 215 are automatically coupled, and the arm 100 and sleeve 215 retract until the head 120 disengages from the arm 100, leaving it in the eyepiece 50.

When the head 120 disengages from the coupled arm/sleeve, the head 120 returns from the second (contracted) position (in which the contact lens 130 is gripped) to the first (extended) position, in which the contact lens 130 rests on and is supported by the head 120. The coupled arm/sleeve continues to retract until it is fully contained within the body 40.

Retention of Eye Lids

The eyelid opening means 70 is activated when a user, looking into the opening 60 of the eyepiece 50, contacts the eyepiece 50 against their eyelids 95. The eyepiece 50 is sprung so that it retracts when pressed against the eyelids 95, and as it retracts the arms of the eyelid opening means 70 can contact the eyelids 95. As the eyepiece 50 fully retracts, the arms of the eyelid opening means 70 move along paths defined by guide tracks 150 such that the eyelids 95 are gently moved into an open position, and retained in that position prior to insertion and removal of a contact lens 130 into or from the eye. The pressure is controlled by the user, helping them feel as though they are in control.

Insertion of Contact Lenses into an Eye

A contact lens 130, immersed within an appropriate storage or cleaning solution within an eyepiece 50 and being positioned on the head 120 of the eyepiece 50 may be inserted into the eye by pressing the button 310 located on the body 40. The user looks into the opening 60 of the eyepiece 50 and the eyelid opening means 70 retains the eyelids 95 in an open position. A single press of the button 310 will trigger the cycle of events which leads to insertion of the contact lens 130 into the eye of the user. The first step is an extension of the arm 100 through the opening 60 until the arm 100 engages the head 120 of the eyepiece 50. The arm 100 extends further until the contact lens 130 contacts the eyeball 160. The extension of the arm 100 is controlled and stopped when the contact lens 130 touches the eyeball 160. Upon contact with the eyeball 160, the contact lens 130 is sucked onto the eyeball 160 through capillary action of the solution on the contact lens 130. After insertion of the contact lens 130, the arm 100 is automatically retracted, disengaging from the head 120, and retracted further until it is fully contained within body 40 of the apparatus 10.

Removal of Contact Lenses from an Eye

Following insertion of a contact lens 130 into an eye, a single press of the button 310 located on the body 40 will trigger the cycle of events which leads to removal of the contact lens 130 from the eye of the user. The user looks into the opening 60 of the eyepiece 50 and the eyelid opening means 70 retains the eyelids 95 in an open position.

Following the pressing of the button, in the first step, the arm 100 and sleeve 215 are automatically coupled, and the coupled arm/sleeve extends through the opening 60 until the arm 100 engages the head 120. The coupled arm/sleeve continues to extend until it contacts the contact lens 130 positioned on the eyeball 160. The extension of the arm 100 is controlled and stopped when the head 120 encounters a programmed amount of resistance as it touches the contact lens 130 positioned on the eyeball 160. The arm/sleeve retracts a short distance, and then the arm 100 and sleeve 215 are uncoupled. The arm 100 then retracts a set distance until the head 120 is deformed from the first (extended) position to the second (contracted) position, thereby gripping the contact lens 130. As the contact lens has been in the eye for a day the moisture content has lowered, resulting in the contact lens 130 becoming tacky to the touch and thereby facilitating the removal process. The arm 100 and the sleeve 215 are then coupled together and they retract until the head 120 is contained within the eyepiece 50, and then the arm 100 continues to retract until it is contained within the body 40, leaving the head 120 (and the contact lens 130) in the eyepiece 50.

Cleaning of Contact Lenses

Cleaning solution is applied to a contact lens 130 contained within an eyepiece 50. The cleaning solutions are held within the cleaning housing 20. The contact lens 130 can be cleaned by engaging the cleaning housing 20 with an eyepiece 50 or eyepieces 50. The eyepiece 50 does not have to be attached to the body 40, although cleaning can be performed if the eyepiece 50 is attached to the body 40. Engaging the cleaning housing 20 with one or more eyepieces 50 or eyepieces 50 creates a seal which prevents the contact lens 130 being exposed to dust or micro-organisms. By pressing the button (not shown) located on the cleaning housing 20, a user activates an electric motor (not shown) which is attached to an off centre gear which causes both rotation of the cleaning heads 270 and a vertically oscillating movement. The cleaning last for approximately 30 seconds, after which the contact lens 130 is clean. The solution is automatically drained out of the eyepiece 50, leaving the contact lens 130 substantially solution free to be inserted into an eye.

Storage of Contact Lenses

Contact lenses may be stored in the eyepiece 50 either before or after cleaning by adding a storage solution (e.g. sterile saline) to the eyepiece 50 to keep the contact lens 130 wet. Prior to insertion into an eye, the contact lenses may be cleaned.

The invention claimed is:

1. An apparatus for manipulation and cleaning of a contact lens, said apparatus comprising an at least one eyepiece, an at least one body, and a cleaning housing, said at least one eyepiece when attached to said at least one body defining an opening into said at least one body and said at least one eyepiece comprising:

(i) a head for engaging a contact lens; and
(ii) an eyelid opening means, said at least one body containing a contact lens manipulation means comprising an elongate arm defining a longitudinal axis and an arm movement means communicating with said arm, said arm movement means effecting movement of said arm between a retracted position and an extended position;

said apparatus arranged such that when said at least one eyepiece is attached to said at least one body and the face of a user is in contact with said at least one eyepiece, an eyeball and upper and lower eyelids of said user being positioned over said opening, said eyelid opening means is engageable with said upper and lower eyelids to retain them open, said arm being engaged with said head and being extendable to contact said eyeball of said user and effect insertion and removal of a contact lens into and from said eye;

said cleaning housing comprising contact lens cleaning means and being engageable with said at least one eyepiece, such that when said at least one eyepiece and said cleaning housing are engaged, said contact lens cleaning means can effect cleaning of a contact lens engaged with said head of said at least one eyepiece.

2. An apparatus according to claim 1, said apparatus comprising two eyepieces, a body and a cleaning housing, said eyepieces being removeably attachable to said body and said cleaning housing being engageable with said eyepieces, such that when at least one eyepiece is engaged with said cleaning housing, said contact lens cleaning means can effect cleaning of any contact lens engaged with said head of said eyepiece.

3. An apparatus according to claim 2, wherein only one of said eyepieces is attachable to said body at a time.

4. An apparatus according to claim 1 wherein said arm is capable of releasably engaging said head.

5. An apparatus according to claim 1 wherein said arm extends through said opening to engage said head.

6. An apparatus according to claim 1 wherein said arm movement means effects movement of said arm between a retracted position in which said arm is contained within said body of said apparatus, and an extended position in which said arm extends through said opening.

7. An apparatus according to claim 1 wherein said arm is attached to said head.

8. An apparatus according to claim 1, wherein said eyelid opening means comprises a plurality of arms, each of said arms being movable within a guide track positioned within said eyepiece, wherein said arms, responsive to contact against said upper and lower eyelids, move along said guide tracks engaging and retaining said upper and lower eyelids in an open position.

9. An apparatus according to claim 1 wherein said contact lens manipulation means comprises a rack associated with said arm, said rack engaging with a worm associated with said arm movement means.

10. An apparatus according to claim 1 wherein said contact lens manipulation means comprises an electric motor to effect movement of said arm between said extended and retracted positions.

11. An apparatus according to claim 1 wherein said head is resiliently deformable between a first extended state and a second contracted state, wherein said head is capable of gripping a contact lens when said head is in said contracted state.

12. An apparatus according to claim 1, said contact lens manipulation means additionally comprising a head manipulating means to effect gripping of said contact lens by said head.

13. An apparatus according to claim 12 wherein said head manipulating means comprises a longitudinally elongate sleeve positioned coaxial with and radially extended from said arm and defining first and second ends, said arm being positioned radially inwards of said sleeve and defining a head-contacting end, said first end of said sleeve terminating adjacent to said head-contacting end of said arm, wherein said head and arm are movable relative to said sleeve along said longitudinal axis between a first position in which said head does not engage said sleeve and is in said first extended state, and a second position in which said head engages said sleeve and is deformed into said second contracted state, thereby effecting gripping of said contact lens.

14. An apparatus according to claim 13, wherein said head manipulating means further comprises a coupling control means, said coupling control means being capable of coupling and uncoupling said sleeve and said arm between coupled and uncoupled states, wherein in said coupled state said arm moves in conjunction with said sleeve, and in said uncoupled state said arm moves independently of said sleeve.

15. A method of inserting or removing at least one contact lens into or from an eye of a user using an apparatus for manipulation of a contact lens, said apparatus comprising an at least one eyepiece, a cleaning housing and an at least one body, said at least one eyepiece when attached to said at least one body defining an opening into said at least one body and said at least one eyepiece comprising:
  (i) a head for engaging a contact lens; and
  (ii) an eyelid opening means,
  said at least one body containing a contact lens manipulation means comprising an elongate arm defining a longitudinal axis and an arm movement means communicating with said arm, said arm movement means effecting movement of said arm between a retracted position and an extended position;
  said apparatus arranged such that when said at least one eyepiece is attached to said at least one body and the face of a user is in contact with said at least one eyepiece, an eyeball and upper and lower eyelids of said user being positioned over said opening, said eyelid opening means is engageable with said upper and lower eyelids to retain them open, said arm being engaged with said head and being extendable to contact said eyeball of said user and effect insertion and removal of a contact lens into and from said eye; said method comprising the steps of:
  (i) contacting the face of a user with said at least one eyepiece, an eyeball and upper and lower eyelids of the user being positioned over said opening;
  (ii) operating said apparatus so as to engage said upper and lower eyelids and retain them open and extend said arm engaged with said head to contact said eyeball of said user and effect insertion or removal of a contact lens into or from said eye;
  (iii) engaging said cleaning housing with said at least one eyepiece having a contact lens engaged with said head; and
  (iv) operating said apparatus so as to effect cleaning of a contact lens engaged with said head of said eyepiece;
  said cleaning housing comprising contact lens cleaning means and being engageable with said eyepiece, such that when said at least one eyepiece and cleaning housing are engaged, said contact lens cleaning means can effect cleaning of a contact lens engaged with said head of said eyepiece.

* * * * *